US00PP29544P2

(12) United States Plant Patent
Danziger

(10) Patent No.: US PP29,544 P2
(45) Date of Patent: Jul. 24, 2018

(54) ***SCAVEOLA* PLANT NAMED 'DSCAVPUHAZ'**

(50) Latin Name: *Scaveola aemula*
Varietal Denomination: DSCAVPUHAZ

(71) Applicant: Gavriel Danziger, Beit Dagan (IL)

(72) Inventor: Gavriel Danziger, Beit Dagan (IL)

(73) Assignee: Danziger 'Dan' Flower Farm (IL)

( * ) Notice: Subject to any disclaimer, the term of this patent is extended or adjusted under 35 U.S.C. 154(b) by 0 days.

(21) Appl. No.: 15/731,259

(22) Filed: May 10, 2017

(51) Int. Cl.
*A01H 5/02* (2018.01)

(52) U.S. Cl.
USPC ..... Plt./363
CPC ..... *A01H 5/02* (2013.01)

(58) Field of Classification Search
USPC ..... Plt./363
CPC ..... A01H 5/02
See application file for complete search history.

*Primary Examiner* — Kent L Bell
(74) *Attorney, Agent, or Firm* — Cassandra Bright

(57) ABSTRACT

A new and distinct *Scaveola* cultivar named 'DSCAVPUHAZ' is disclosed, characterized by a dark purple flower color. The plant has a strong, sturdy foliage and a unique semi-trailing and upright habit. The variety is characterized by early and abundant flowering. The new variety is a *Scaevola*, normally produced as an outdoor garden or container plant.

2 Drawing Sheets

Figure 1:
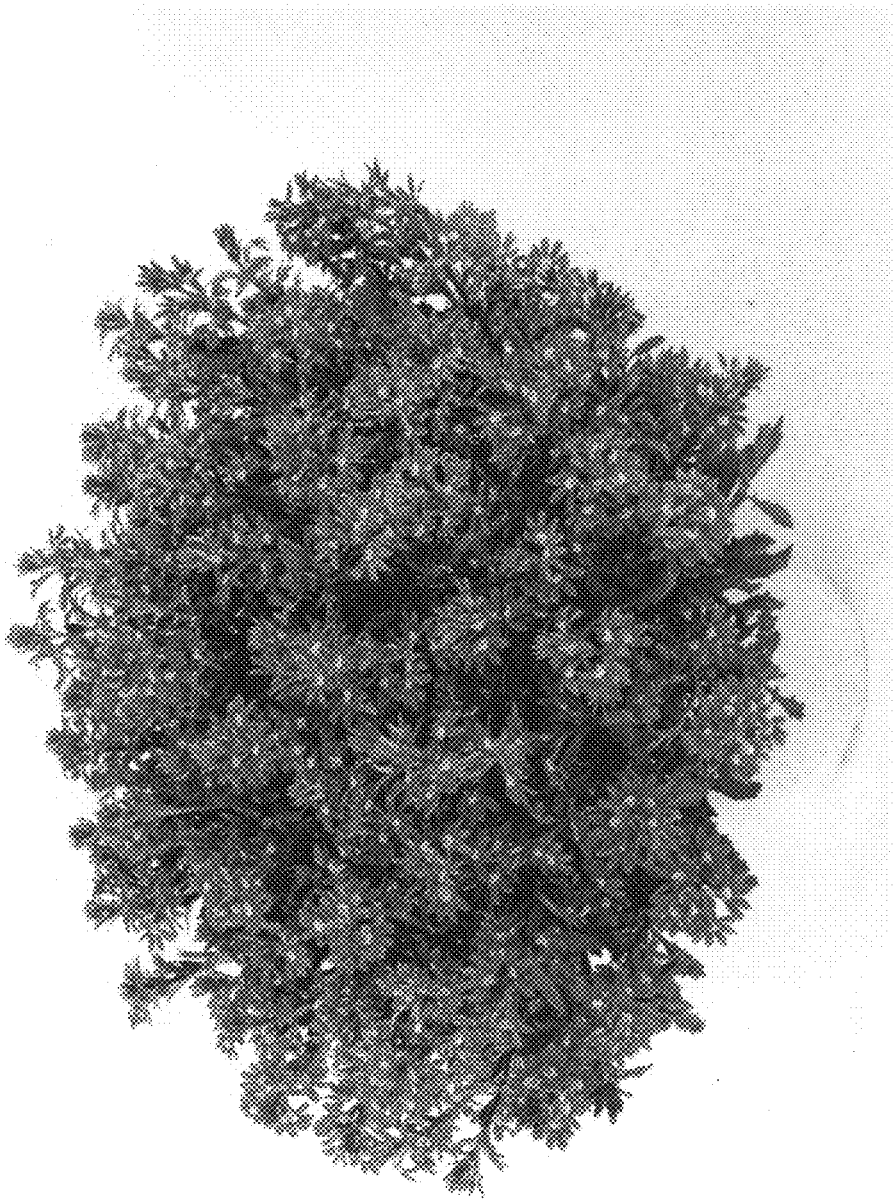

Latin name of the genus and species: *Scaveola aemula.*
Variety denomination: 'DSCAVPUHAZ'.

BACKGROUND OF THE INVENTION

The new *Scaveola* cultivar is the product of a planned breeding program conducted by the inventor, Gavriel Danziger, in Moshav Mishmar Hashiva, Israel. The objective of the breeding program was to produce new *Scaveola* varieties with denser plant habits, strong garden performance, in a range of flower colors. The cross resulting in this new variety was made in 2014.

The seed parent is the unpatented *Scaveola* 'cv. 1-1'. The pollen parent is the unpatented, proprietary variety *Scaveola* 'cv 6-367'. The new variety was identified as a potentially interesting selection in October 2006, at a research greenhouse in Moshav Mishmar Hashiva, Israel. Further observations and evaluations were made during 2007.

Asexual reproduction of the new cultivar 'DSCAVPUHAZ' by vegetative cuttings was first performed during 2007, at a research greenhouse in Wonga Park. Subsequent propagation has shown that the unique features of this cultivar are stable and reproduced true to type in successive generations.

SUMMARY OF THE INVENTION

The cultivar 'DSCAVPUHAZ' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DSCAVPUHAZ' These characteristics in combination distinguish 'DSCAVPUHAZ' as a new and distinct *Scaveola* cultivar:

1. Dark purple color.
2. Strong and sturdy foliage.
3. Distinctive semi-trailing and upright habit.

4. Early flowering.
5. Abundant flowering.

PARENT COMPARISON

Plants of the new cultivar 'DSCAVPUHAZ' are similar to plants of the seed parent, 'cv. 1-1' in most horticultural characteristics, however, plants of the new cultivar 'DSCAVPUHAZ' differ in the following;

1. The new variety has a darker flower color than the seed parent.
2. The new variety is more vigorous than the seed parent.
3. The new variety has smaller leaves than the seed parent.

Plants of the new cultivar 'DSCAVPUHAZ' are similar to plants of the pollen parent, 'cv. 6-367' in most horticultural characteristics, however, plants of the new cultivar 'DSCAVPUHAZ' differ in the following;

1. The new variety has a semi-trailing habit while the pollen parent has a trailing habit.
2. The new variety has a darker flower color than the pollen parent.
3. The new variety is more vigorous than the pollen parent.
4. The new variety has larger flowers than the pollen parent.

COMMERCIAL COMPARISON

Plants of the new cultivar can be compared to the unpatented commercial variety 'Pink Charm'. These varieties are similar in most horticultural characteristics; however, 'DSCAVPUHAZ' differs in the following:

1. The new variety has a dark purple flower, while 'Pink Charm' is pink.
2. The new has a unique semi-trailing and upright habit, while 'Pink Charm' is completely semi trailing in habit.

Plants of the new cultivar are best compared to the commercial variety 'Blue Sea'. These varieties are similar in most horticultural characteristics; however, 'DSCAVPUHAZ' differs in the following:

1. The new variety has unique semi-trailing and upright habit. 'Blue Sea' has trailing habit.
2. The new variety has dark purple flowers. 'Blue Sea' has blue flowers.
3. The foliage of the new variety is less sensitive to cold than foliage of 'Blue Sea'.
4. The new variety is less vigorous than 'Blue Sea'.

BRIEF DESCRIPTION OF THE PHOTOGRAPHS

The accompanying photograph in FIG. 1 illustrates in full color a typical plant of 'DSCAVPUHAZ'.

Figure 2:
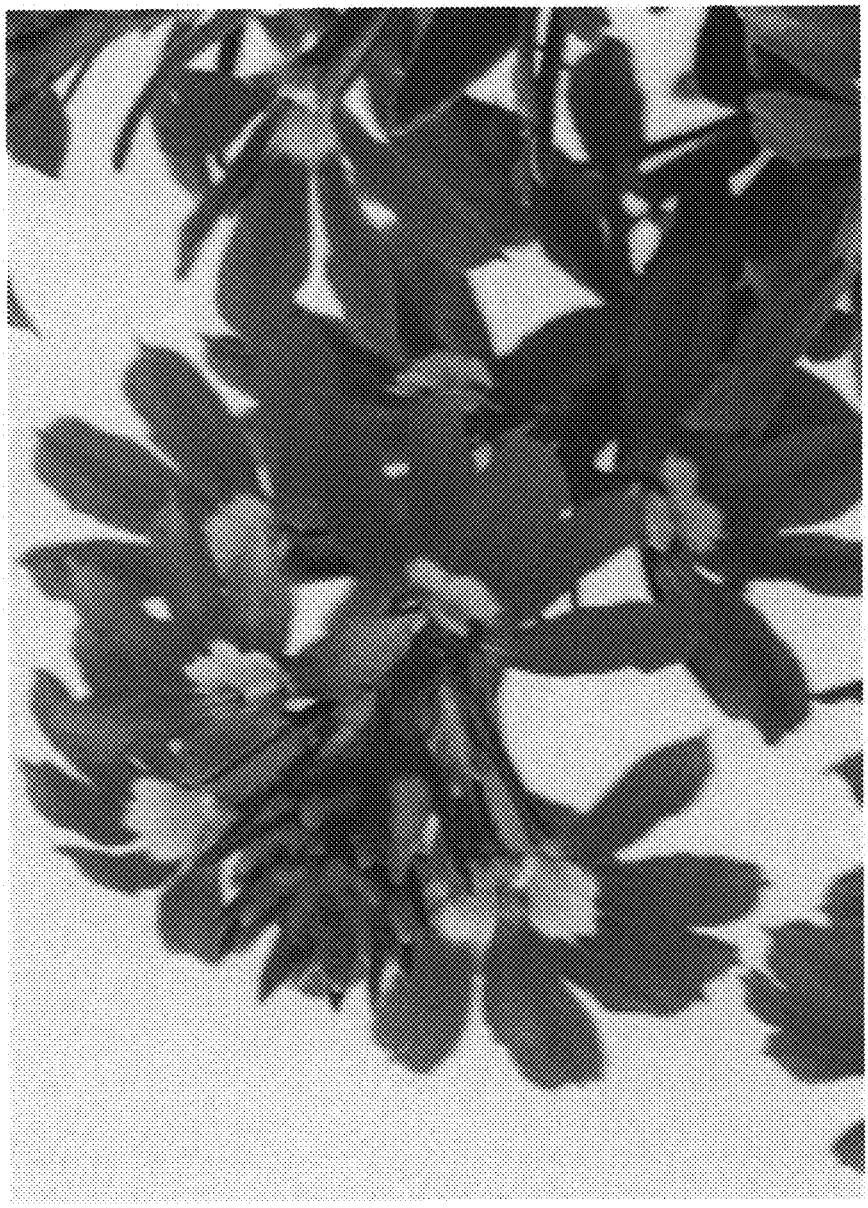

FIG. 2 illustrates in full color a typical flower of 'DSCAVPUHAZ' grown in a greenhouse, in Moshav Mishmar Hashiva, in a 15 cm pot. Age of the plant photographed is approximately 6 months from an unrooted cutting.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Mini Chart, 2005 except where general terms of ordinary dictionary significance are used. The following observations and measurements describe 'DSCAVPUHAZ' plants grown in a greenhouse in Moshav Mishmar Hashiva. The growing temperature ranged from 15° C. to 28° C. during the day and 10° C. to 15° C. at night. The greenhouse is un-shaded, giving bright, normal sunlight conditions. Measurements and numerical values represent averages of typical plant types.

Botanical classification: *Scaveola aemula* 'DSCAVPUHAZ'.

PROPAGATION

Time to initiate roots: About 16-21 days at approximately 18° C.

Root description: Fine, densely fibrous. Tan to brown, not accurately measured with the R.H.S. chart.

Time to produce a rooted cutting: About 30 days at 18° C.

PLANT

Growth habit: Semi-trailing-upright.
Age of plant described: 6 months.
Container size: 13 cm pot.
Height: 17 cm.
Plant spread: 45-50 cm.
Quantity of lateral branches: 10-15.
Lateral branch description:
- *Diameter*.—Approximately 0.4 cm.
- *Length*.—26 cm.
- *Texture*.—Smooth.
- *Color*.—Near Yellow-Green 144A.

Branches-old wood: Not relevant.
Internode length: Average 1.5 cm.

FOLIAGE

Leaf:
- *Arrangement*.—Alternate.
- *Quantity*.—Approximately 15-20 fully expanded per main branch.
- *Average length*.—Approximately 5 cm.
- *Average width*.—Approximately 1.5 cm.
- *Shape of blade*.—Runcinate.
- *Apex*.—Blunt, Dentate
- *Base*.—Cuneate.
- *Attachment*.—Petiolate.
- *Margin*.—Dentate.
- *Texture of top surface*.—Rough.
- *Texture of bottom surface*.—Rough.
- *Color*.—Young foliage upper side: Near 137A. Young foliage under side: Near 144A. Mature foliage upper side: Near 137B. Mature foliage under side: Near 146B.
- *Venation*.—Type: Only midrib and 2 secondary veins visible. Venation color upper side: Near Yellow-Green 144B. Venation color under side: Near Yellow-Green 146B.
- *Petiole*.—Length: 1.5-2 cm. Width: 1.5 cm. Color: Near Yellow-Green 146C. Texture: Glabrous. Strength: Firm and somewhat flexible.

FLOWER

Natural flowering season: Spring-summer-autumn.
Inflorescence type and habit: Flowers single occurring from leaf axils. Clustered at terminus.
Flower longevity on plant: About 20 days.
Quantity of flowers: 200-250 per plant.
Individual flowers:
Size:
- *Diameter*.—Approximately 3 cm.
- *Length*.—Approximately 2.6-2.8 cm.
- *Persistence*.—Non-persistent.
- *Fragrance*.—None.

Corolla:
- *Petal arrangement*.—5 petals, fused from base, to approximately 50% of length, forming a half tube. Separated portion radiating into a semi-circle/fan shape.
- *Margin*.—Entire.
- *Apex*.—Abruptly acute.
- *Shape*.—Oblong.
- *Length*.—1.3-1.5 cm. Unfused portion: 0.3 cm. Half Tube: 1 cm.
- *Width*.—Unfused portion: 0.1 cm. Half Tube: 0.3-0.5 cm.
- *Texture*.—Velvety all surfaces.

Color:
- *Separate petals*.—When opening: Upper surface: Near Violet-Blue N89C. Lower surface: Near Violet-Blue N89D. Fully opened: Upper surface: Near Violet-Blue 90A. Lower surface: Near Violet-Blue 90B. Fading: Upper surface: Near Violet-Blue 90C. Lower surface: Near Violet-Blue 90D.

Color:
- *Half-tube*.—When opening: Upper surface: Near Yellow 3A. Lower surface: Near Yellow 4C. Fully opened: Upper surface: Near 3A. Lower surface: Near 4C. Fading: Upper surface: Near 3B. Lower surface: Near 4D.

Bud:
*Shape*.—Fusiform.
*Length*.—Approximately 1.5 cm.
*Diameter*.—Approximately 0.3 cm.
*Color*.—Near Green 142C.
Calyx:
*Length*.—Approximately 0.3 cm.
*Diameter*.—Approximately 0.15 cm.
Sepals:
*Quantity*.—2.
*Shape*.—Ligulate.
*Length*.—0.7 cm.
*Width*.—0.1 cm.
*Margin*.—Entire.
*Apex*.—Acute.
*Texture*.—Rugged. Color: Near RHS Green 137D. Mature: Near RHS 137C.
Pedicel:
*Length*.—Average 0.2 cm.
*Diameter*.—0.1 cm.
*Color*.—Near Green 141D.
*Orientation*.—Approximately 45° angle from attachment.
*Strength*.—Good.
*Texture*.—Glabrous.
Fragrance: None.

REPRODUCTIVE ORGANS

Stamens:
*Number*.—5.
*Filament length*.—Approximately 0.4 cm.
*Filament color*.—Near Yellow 5A.
Anthers:
*Shape*.—Ligulate.
*Length*.—Approximately 15-20 mm.
*Color*.—Near Greyed-Orange 177A.
*Pollen*.—Scant quantity, colored near Yellow 9D.
Pistil:
*Number*.—1.
*Length*.—Approximately 1.5 cm.
*Style*.—Length: Approximately 1.0 cm. Color: Near Greyed-Orange 177A.
*Stigma*.—Shape: Oblate. Texture: Hairy, Pilose. Color: Near Greyed-Orange 177B with White 155C tip. Ovary color: Near Yellow-Green 145B.

OTHER CHARACTERISTICS

Seeds and fruits: Low fertility. One ellipsoid black seed 2 mm diameter 4 mm long per flower.
Disease/pest resistance: Neither resistance nor susceptibility to normal diseases and pests of *Scaevola* has been observed.
Temperature tolerance: Temperature range: Observed to tolerate temperatures from 5° C. to at 45° C.

What is claimed is:

1. A new and distinct cultivar of *Scaveola* plant named 'DSCAVPUHAZ' as herein illustrated and described.

* * * * *